United States Patent
Cotton et al.

(10) Patent No.: US 11,458,044 B2
(45) Date of Patent: *Oct. 4, 2022

(54) WOUND DRESSING

(71) Applicant: ConvaTec Technologies Inc., Las Vegas, NV (US)

(72) Inventors: Stephen Michael Cotton, Papplewick (GB); Bryony Jayne Lee, Deeside (GB)

(73) Assignee: ConvaTec Technologies Inc., Las Vegas, NV (US)

(*) Notice: Subject to any disclaimer, the term of this patent is extended or adjusted under 35 U.S.C. 154(b) by 385 days.

This patent is subject to a terminal disclaimer.

(21) Appl. No.: 16/140,438

(22) Filed: Sep. 24, 2018

(65) Prior Publication Data

US 2019/0021912 A1 Jan. 24, 2019

Related U.S. Application Data

(63) Continuation of application No. 13/120,733, filed as application No. PCT/GB2009/002342 on Sep. 29, 2009, now Pat. No. 10,117,783.

(30) Foreign Application Priority Data

Sep. 29, 2008 (GB) ...................... 0817796

(51) Int. Cl.
*A61F 13/02* (2006.01)
*A61F 13/00* (2006.01)

(52) U.S. Cl.
CPC ............... *A61F 13/0203* (2013.01); *A61F 2013/00753* (2013.01)

(58) Field of Classification Search
CPC .............. A61F 13/0203; A61F 13/0213; A61F 13/0206; A61F 13/0209; A61F 2013/00753

See application file for complete search history.

(56) References Cited

U.S. PATENT DOCUMENTS 3,367,333 A * 2/1968 Scheier ............. A61F 13/49003
604/378
4,773,238 A 9/1988 Zafiroglu
(Continued)

FOREIGN PATENT DOCUMENTS

EP 0130061 B1 8/1988
EP 0092999 B1 4/1992
(Continued)

OTHER PUBLICATIONS

Structure, 2017, The George Washington University Museum The Textile Museum (Year: 2017).*

(Continued)

*Primary Examiner* — Catharine L Anderson
*Assistant Examiner* — Arjuna P Chatrathi
(74) *Attorney, Agent, or Firm* — Taft Stettinius & Hollister LLP; Ryan O. White; Derek B. Lavender

(57) ABSTRACT

A wound dressing including a nonwoven absorbent layer including a layer of fabric comprising gel-forming fibers. The absorbent layer is gathered in a longitudinal direction by stitching through the layer of fabric using one or more resilient threads or yarns and an inelastic thread or yarn. The resilient and inelastic threads or yarns gather the layer of fabric so that the layer of fabric in use is configured to maintain close conformability with a wound during movement, and to elongate by 35% to 85% and then recover.

19 Claims, 2 Drawing Sheets

(56) References Cited

U.S. PATENT DOCUMENTS

Figure 1:
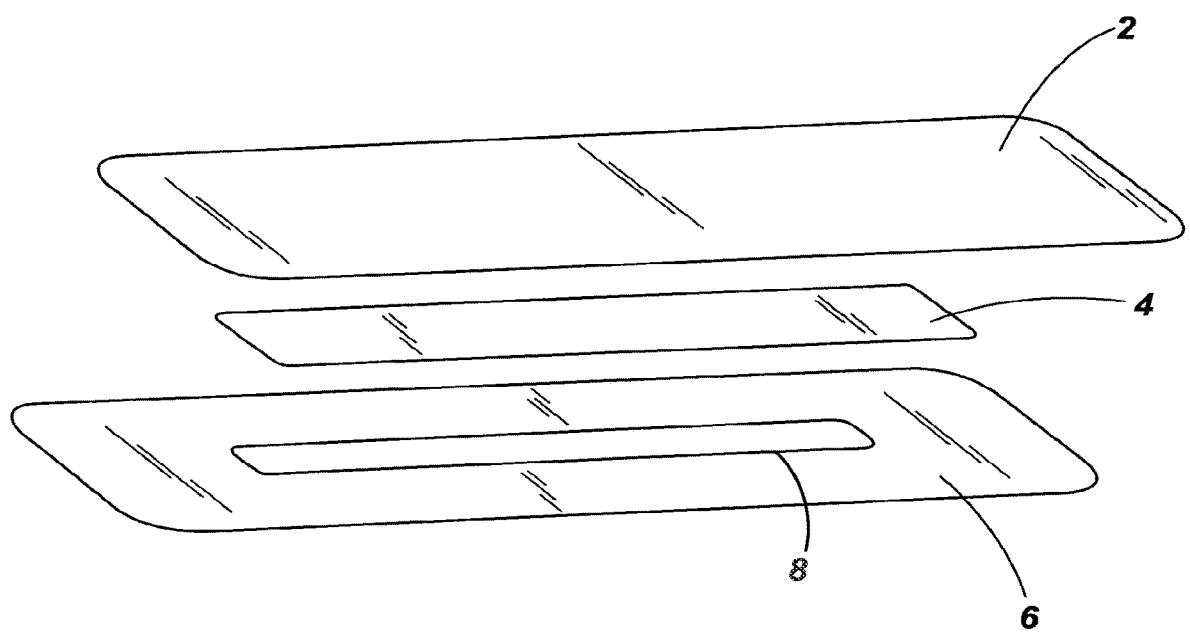

| | | | |
|---|---|---|---|
| 4,891,957 A | 1/1990 | Strack et al. | |
| 4,957,795 A | 9/1990 | Riedel | |
| 5,203,186 A * | 4/1993 | Zafiroglu | D04B 21/165 428/102 |
| 5,308,673 A * | 5/1994 | Tochacek | D04B 21/165 428/326 |
| 5,623,888 A * | 4/1997 | Zafiroglu | D04B 21/165 428/152 |
| 5,647,842 A | 7/1997 | Kininmonth et al. | |
| 6,233,795 B1 | 5/2001 | Dischler | |
| 6,267,744 B1 * | 7/2001 | Roberts | A61F 13/00038 602/76 |
| 6,555,730 B1 * | 4/2003 | Albrod | A61L 15/58 602/76 |
| 10,016,537 B2 | 7/2018 | Menon et al. | |
| 10,046,096 B2 | 8/2018 | Askem et al. | |
| 10,076,447 B2 | 9/2018 | Barta et al. | |
| 10,076,587 B2 | 9/2018 | Locke et al. | |
| 10,117,783 B2 * | 11/2018 | Cotton | A61F 13/0203 |
| 10,143,784 B2 | 12/2018 | Walton et al. | |
| 10,426,670 B2 | 10/2019 | Von Blucher et al. | |
| 10,426,747 B2 | 10/2019 | Johnson | |
| 10,426,874 B2 | 10/2019 | Chien et al. | |
| 10,426,875 B2 | 10/2019 | Blott et al. | |
| 10,426,938 B2 | 10/2019 | Locke et al. | |
| 10,434,015 B2 | 10/2019 | Taylor et al. | |
| 10,434,142 B2 | 10/2019 | Niazi et al. | |
| 10,434,210 B2 | 10/2019 | Olson et al. | |
| 10,434,284 B2 | 10/2019 | Hanson et al. | |
| 10,449,094 B2 | 10/2019 | Donda et al. | |
| D866,756 S | 11/2019 | Allen et al. | |
| 10,463,760 B2 | 11/2019 | Karthikeyan et al. | |
| 10,463,773 B2 | 11/2019 | Haggstrom et al. | |
| 10,470,933 B2 | 11/2019 | Riesinger | |
| 10,470,936 B2 | 11/2019 | Wohlgemuth et al. | |
| 10,471,122 B2 | 11/2019 | Shi et al. | |
| 10,471,190 B2 | 11/2019 | Locke et al. | |
| 10,478,345 B2 | 11/2019 | Barta et al. | |
| 10,478,346 B2 | 11/2019 | Knutson | |
| 10,478,394 B2 | 11/2019 | Yu | |
| 10,485,707 B2 | 11/2019 | Sexton | |
| 10,485,891 B2 | 11/2019 | Andrews et al. | |
| 10,485,892 B2 | 11/2019 | Hands et al. | |
| 10,485,906 B2 | 11/2019 | Freedman et al. | |
| 10,486,135 B2 | 11/2019 | Yang et al. | |
| 10,492,956 B2 | 12/2019 | Zamierowski | |
| 10,493,178 B2 | 12/2019 | Marchant et al. | |
| 10,493,184 B2 | 12/2019 | Collinson et al. | |
| 10,493,185 B2 | 12/2019 | Stokes et al. | |
| 10,500,099 B2 | 12/2019 | Hung et al. | |
| 10,500,103 B2 | 12/2019 | Croizat et al. | |
| 10,500,104 B2 | 12/2019 | Sookraj | |
| 10,500,173 B2 | 12/2019 | Yang et al. | |
| 10,500,235 B2 | 12/2019 | Wardell | |
| 10,500,300 B2 | 12/2019 | Dybe et al. | |
| 10,500,301 B2 | 12/2019 | Laurensou | |
| 10,500,302 B2 | 12/2019 | Holm et al. | |
| 10,501,487 B2 | 12/2019 | Andrews et al. | |
| 10,506,928 B2 | 12/2019 | Locke et al. | |
| 10,507,141 B2 | 12/2019 | Allen et al. | |
| 10,507,259 B2 | 12/2019 | Cree et al. | |
| 10,512,707 B2 | 12/2019 | Whalen, III et al. | |
| 10,525,170 B2 | 1/2020 | Havenstrite et al. | |
| 10,532,137 B2 | 1/2020 | Pratt et al. | |
| 10,532,194 B2 | 1/2020 | Locke et al. | |
| 10,537,657 B2 | 1/2020 | Phillips et al. | |
| 10,542,936 B2 | 1/2020 | Goldberg et al. | |
| 10,543,133 B2 | 1/2020 | Shaw et al. | |
| 10,543,293 B2 | 1/2020 | Suschek | |
| 10,548,777 B2 | 2/2020 | Locke et al. | |
| 10,549,008 B2 | 2/2020 | Yoo | |
| 10,549,016 B2 | 2/2020 | Bushko et al. | |
| 10,549,017 B2 | 2/2020 | Hsiao et al. | |
| 10,555,838 B2 | 2/2020 | Wu et al. | |
| 10,555,839 B2 | 2/2020 | Hartwell | |
| 10,556,044 B2 | 2/2020 | Robinson et al. | |
| 10,561,533 B2 | 2/2020 | Hoggarth et al. | |
| 10,561,536 B2 | 2/2020 | Holm et al. | |
| 10,568,767 B2 | 2/2020 | Addison et al. | |
| 10,568,768 B2 | 2/2020 | Long et al. | |
| 10,568,770 B2 | 2/2020 | Robinson et al. | |
| 10,568,771 B2 | 2/2020 | MacDonald et al. | |
| 10,568,773 B2 | 2/2020 | Tuck et al. | |
| 10,568,983 B2 | 2/2020 | Gerdes et al. | |
| 10,575,991 B2 | 3/2020 | Dunn | |
| 10,575,992 B2 | 3/2020 | Sarangapani | |
| 10,576,037 B2 | 3/2020 | Harrell | |
| 10,576,189 B2 | 3/2020 | Locke et al. | |
| 10,583,042 B2 | 3/2020 | Sarangapani et al. | |
| 10,583,228 B2 | 3/2020 | Shuler et al. | |
| 10,589,007 B2 | 3/2020 | Coulthard et al. | |
| 10,590,184 B2 | 3/2020 | Kuo | |
| 10,610,414 B2 | 4/2020 | Hartwell et al. | |
| 10,610,415 B2 | 4/2020 | Griffey et al. | |
| 10,610,623 B2 | 4/2020 | Robinson et al. | |
| 10,617,569 B2 | 4/2020 | Bonn | |
| 10,617,608 B2 | 4/2020 | Shin et al. | |
| 10,617,769 B2 | 4/2020 | Huang | |
| 10,617,784 B2 | 4/2020 | Yu et al. | |
| 10,617,786 B2 | 4/2020 | Kluge et al. | |
| 10,618,266 B2 | 4/2020 | Wright et al. | |
| 10,624,984 B2 | 4/2020 | Courage et al. | |
| 10,625,002 B2 | 4/2020 | Locke et al. | |
| 10,632,019 B2 | 4/2020 | Vitaris | |
| 10,632,224 B2 | 4/2020 | Hardy et al. | |
| 10,639,206 B2 | 5/2020 | Hu et al. | |
| 10,639,350 B2 | 5/2020 | Arber et al. | |
| 10,639,404 B2 | 5/2020 | Lichtenstein | |
| 10,646,614 B2 | 5/2020 | Grinstaff et al. | |
| 10,653,562 B2 | 5/2020 | Robinson et al. | |
| 10,653,782 B2 | 5/2020 | Ameer et al. | |
| 10,653,810 B2 | 5/2020 | Datt et al. | |
| 10,653,821 B2 | 5/2020 | Nichols | |
| 10,653,823 B2 | 5/2020 | Bharti et al. | |
| 10,660,799 B2 | 5/2020 | Wu et al. | |
| 10,660,851 B2 | 5/2020 | Millis et al. | |
| 10,660,992 B2 | 5/2020 | Canner et al. | |
| 10,660,994 B2 | 5/2020 | Askem et al. | |
| 10,667,955 B2 | 6/2020 | Allen et al. | |
| 10,667,956 B2 | 6/2020 | Van Holten et al. | |
| 10,682,257 B2 | 6/2020 | Lu | |
| 10,682,258 B2 | 6/2020 | Manwaring et al. | |
| 10,682,259 B2 | 6/2020 | Hunt et al. | |
| 10,682,318 B2 | 6/2020 | Twomey et al. | |
| 10,682,386 B2 | 6/2020 | Ellis-Behnke et al. | |
| 10,682,446 B2 | 6/2020 | Askem et al. | |
| 10,687,983 B2 | 6/2020 | Dahlberg et al. | |
| 10,687,985 B2 | 6/2020 | Lee et al. | |
| 10,688,215 B2 | 6/2020 | Munro et al. | |
| 10,688,217 B2 | 6/2020 | Hanson et al. | |
| RE48,117 E | 7/2020 | Albert et al. | |
| 10,702,419 B2 | 7/2020 | Locke et al. | |
| 10,702,420 B2 | 7/2020 | Hammond et al. | |
| 10,703,942 B2 | 7/2020 | Tunius | |
| 10,709,760 B2 | 7/2020 | Gronberg et al. | |
| 10,709,807 B2 | 7/2020 | Kshirsagar | |
| 10,709,883 B2 | 7/2020 | Spector | |
| 10,716,711 B2 | 7/2020 | Locke et al. | |
| 10,716,874 B2 | 7/2020 | Koyama et al. | |
| 10,729,589 B2 | 8/2020 | Dorian et al. | |
| 10,729,590 B2 | 8/2020 | Simmons et al. | |
| 10,729,826 B2 | 8/2020 | Lin | |
| 10,736,787 B2 | 8/2020 | Hannigan et al. | |
| 10,736,788 B2 | 8/2020 | Locke et al. | |
| 10,736,985 B2 | 8/2020 | Odermatt et al. | |
| 10,737,003 B2 | 8/2020 | Fujisaki | |
| 10,743,900 B2 | 8/2020 | Ingram et al. | |
| 10,744,040 B2 | 8/2020 | Kazala, Jr. et al. | |
| 10,744,041 B2 | 8/2020 | Hartwell | |
| 10,744,225 B2 | 8/2020 | Lindgren et al. | |
| 10,744,237 B2 | 8/2020 | Guidi et al. | |
| 10,744,238 B2 | 8/2020 | Guidi et al. | |
| 10,744,239 B2 | 8/2020 | Armstrong et al. | |

(56) References Cited

U.S. PATENT DOCUMENTS

| | | | |
|---|---|---|---|
| 10,744,240 B2 | 8/2020 | Simmons et al. |
| 10,751,212 B2 | 8/2020 | Raza et al. |
| 10,751,442 B2 | 8/2020 | Bonnefin et al. |
| 10,751,452 B2 | 8/2020 | Topaz |
| 10,758,423 B2 | 9/2020 | Pigg et al. |
| 10,758,424 B2 | 9/2020 | Blott et al. |
| 10,758,425 B2 | 9/2020 | Blott et al. |
| 10,758,426 B2 | 9/2020 | Eddy |
| 10,758,651 B2 | 9/2020 | Blott et al. |
| 10,765,561 B2 | 9/2020 | Lattimore et al. |
| 10,765,783 B2 | 9/2020 | Locke et al. |
| 10,772,767 B2 | 9/2020 | Bjork et al. |
| 10,772,999 B2 | 9/2020 | Svensby |
| 10,779,993 B2 | 9/2020 | Bishop et al. |
| 10,780,114 B2 | 9/2020 | Udagawa et al. |
| 10,780,194 B2 | 9/2020 | Flach et al. |
| 10,780,201 B2 | 9/2020 | Lin |
| 10,780,202 B2 | 9/2020 | Askem et al. |
| 10,780,203 B2 | 9/2020 | Coulthard et al. |
| 10,782,238 B2 | 9/2020 | Hicks et al. |
| 10,792,191 B2 | 10/2020 | Robinson et al. |
| 10,792,192 B2 | 10/2020 | Tout et al. |
| 10,792,337 B2 | 10/2020 | Leung et al. |
| 10,792,404 B2 | 10/2020 | Hu et al. |
| 10,792,482 B2 | 10/2020 | Randolph et al. |
| 10,800,905 B2 | 10/2020 | Delli-Santi et al. |
| 10,806,819 B2 | 10/2020 | Shuler |
| 2003/0040691 A1* | 2/2003 | Griesbach, III .......... B32B 5/26 602/45 |
| 2005/0015068 A1 | 1/2005 | Bean et al. |
| 2006/0089614 A1 | 4/2006 | Bonnin |
| 2006/0127462 A1 | 6/2006 | Canada et al. |
| 2006/0155260 A1 | 7/2006 | Blott et al. |
| 2006/0172000 A1 | 8/2006 | Cullen et al. |
| 2006/0253058 A1* | 11/2006 | Evans ................. A61F 13/0273 602/41 |
| 2007/0042024 A1* | 2/2007 | Gladman ................ A61L 15/60 424/445 |
| 2007/0160654 A1 | 7/2007 | Ferguson |
| 2007/0173162 A1 | 7/2007 | Ethiopia et al. |
| 2007/0185426 A1 | 8/2007 | Ambrosio et al. |
| 2007/0219512 A1 | 9/2007 | Heaton et al. |
| 2007/0225663 A1* | 9/2007 | Watt ........................ A61M 1/90 602/42 |
| 2007/0239078 A1 | 10/2007 | Jaeb |
| 2009/0234307 A1 | 9/2009 | Vitaris |
| 2009/0259203 A1 | 10/2009 | Hu et al. |
| 2009/0293887 A1 | 12/2009 | Wilkes et al. |
| 2009/0299303 A1 | 12/2009 | Seegert |
| 2010/0015208 A1 | 1/2010 | Kershaw et al. |
| 2010/0030178 A1 | 2/2010 | MacMeccan et al. |
| 2010/0125233 A1 | 5/2010 | Edward S. et al. |
| 2010/0125258 A1 | 5/2010 | Coulthard et al. |
| 2010/0137775 A1 | 6/2010 | Hu et al. |
| 2010/0185163 A1 | 7/2010 | Heagle |
| 2010/0298790 A1 | 11/2010 | Guidi et al. |
| 2011/0015595 A1 | 1/2011 | Robinson et al. |
| 2011/0028918 A1 | 2/2011 | Hartwell |
| 2011/0112457 A1 | 5/2011 | Holm et al. |
| 2011/0178451 A1 | 7/2011 | Robinson et al. |
| 2011/0224593 A1 | 9/2011 | Tunius |
| 2011/0224630 A1 | 9/2011 | Simmons et al. |
| 2011/0230849 A1 | 9/2011 | Coulthard et al. |
| 2011/0251566 A1 | 10/2011 | Zimnitsky et al. |
| 2011/0257572 A1 | 10/2011 | Locke et al. |
| 2011/0257573 A1 | 10/2011 | Hong et al. |
| 2011/0275972 A1 | 11/2011 | Rosenberg |
| 2012/0071845 A1 | 3/2012 | Hu et al. |
| 2012/0130332 A1 | 5/2012 | Cotton et al. |
| 2012/0136325 A1 | 5/2012 | Allen et al. |
| 2012/0209226 A1 | 8/2012 | Simmons et al. |
| 2013/0053795 A1 | 2/2013 | Coulthard et al. |
| 2013/0123728 A1 | 5/2013 | Pratt et al. |
| 2013/0226063 A1 | 8/2013 | Taylor et al. |
| 2014/0005618 A1 | 1/2014 | Locke et al. |
| 2014/0074053 A1 | 3/2014 | Locke et al. |
| 2014/0188060 A1 | 7/2014 | Robinson et al. |
| 2014/0194838 A1 | 7/2014 | Wibaux et al. |
| 2014/0200532 A1 | 7/2014 | Robinson et al. |
| 2014/0236112 A1 | 8/2014 | Von Wolff et al. |
| 2014/0256925 A1 | 9/2014 | Catchmark et al. |
| 2014/0276499 A1 | 9/2014 | Locke et al. |
| 2014/0296804 A1 | 10/2014 | Hicks et al. |
| 2014/0308338 A1 | 10/2014 | Nierle et al. |
| 2014/0309574 A1 | 10/2014 | Cotton |
| 2015/0018433 A1 | 1/2015 | Leipzig et al. |
| 2015/0057624 A1 | 2/2015 | Simmons et al. |
| 2015/0071985 A1 | 3/2015 | Walker et al. |
| 2015/0079152 A1 | 3/2015 | Wuollett et al. |
| 2015/0094674 A1 | 4/2015 | Pratt et al. |
| 2015/0104486 A1 | 4/2015 | Bonnefin et al. |
| 2015/0112311 A1 | 4/2015 | Hammond et al. |
| 2015/0119831 A1 | 4/2015 | Robinson et al. |
| 2015/0119834 A1 | 4/2015 | Locke et al. |
| 2015/0141941 A1 | 5/2015 | Allen et al. |
| 2015/0148785 A1 | 5/2015 | Kleiner |
| 2015/0174304 A1 | 6/2015 | Askem et al. |
| 2015/0245949 A1 | 9/2015 | Locke et al. |
| 2015/0246164 A1 | 9/2015 | Heaton et al. |
| 2015/0250979 A1 | 9/2015 | Loske |
| 2015/0265741 A1 | 9/2015 | Duncan et al. |
| 2015/0265743 A1 | 9/2015 | Hanson et al. |
| 2015/0320901 A1 | 11/2015 | Chandrashekhar-Bhat et al. |
| 2016/0008293 A1 | 1/2016 | Shi et al. |
| 2016/0038626 A1 | 2/2016 | Locke et al. |
| 2016/0051724 A1 | 2/2016 | Sahin et al. |
| 2016/0067107 A1 | 3/2016 | Cotton |
| 2016/0100987 A1 | 4/2016 | Hartwell et al. |
| 2016/0106878 A1 | 4/2016 | Yang et al. |
| 2016/0106892 A1 | 4/2016 | Hartwell |
| 2016/0166422 A1 | 6/2016 | Karim et al. |
| 2016/0193244 A1 | 7/2016 | Ota et al. |
| 2016/0222548 A1 | 8/2016 | Agboh |
| 2016/0271178 A1 | 9/2016 | Hauser et al. |
| 2016/0287743 A1 | 10/2016 | Andrews |
| 2016/0339158 A1 | 11/2016 | Collinson et al. |
| 2016/0374847 A1 | 12/2016 | Lachenbruch et al. |
| 2017/0014275 A1 | 1/2017 | Schneider |
| 2017/0049111 A1 | 2/2017 | Patton et al. |
| 2017/0072669 A1 | 3/2017 | Sekido et al. |
| 2017/0128269 A1 | 5/2017 | Coulthard et al. |
| 2017/0189237 A1 | 7/2017 | Locke et al. |
| 2017/0189575 A1 | 7/2017 | Lee et al. |
| 2017/0209615 A1 | 7/2017 | Tornero Garcia et al. |
| 2017/0232161 A1 | 8/2017 | Fewkes et al. |
| 2017/0258956 A1 | 9/2017 | Flach et al. |
| 2017/0367895 A1 | 12/2017 | Holm et al. |
| 2017/0368239 A1 | 12/2017 | Askem et al. |
| 2018/0008742 A1 | 1/2018 | Hoggarth et al. |
| 2018/0014974 A1 | 1/2018 | Hoggarth et al. |
| 2018/0023217 A1 | 1/2018 | Patton et al. |
| 2018/0030321 A1 | 2/2018 | Tunius |
| 2018/0042789 A1 | 2/2018 | Bradford et al. |
| 2018/0078423 A1 | 3/2018 | Magin et al. |
| 2018/0086903 A1 | 3/2018 | Zhang et al. |
| 2018/0118809 A1 | 5/2018 | Mearns Spragg |
| 2018/0133066 A1 | 5/2018 | Ahsani et al. |
| 2018/0140467 A1 | 5/2018 | Hunt |
| 2018/0140822 A1 | 5/2018 | Robinson et al. |
| 2018/0200414 A1 | 7/2018 | Askem et al. |
| 2018/0221531 A1 | 8/2018 | Bender et al. |
| 2018/0236124 A1 | 8/2018 | Young et al. |
| 2018/0243463 A1 | 8/2018 | Chatterjee et al. |
| 2018/0243464 A1 | 8/2018 | Hwang et al. |
| 2018/0244857 A1 | 8/2018 | Lee et al. |
| 2018/0272052 A1 | 9/2018 | Locke et al. |
| 2018/0296397 A1 | 10/2018 | Askem et al. |
| 2018/0303873 A1 | 10/2018 | Been et al. |
| 2018/0311419 A1 | 11/2018 | Locke et al. |
| 2018/0333522 A1 | 11/2018 | Pratt et al. |
| 2018/0344533 A1 | 12/2018 | Rovaniemi |
| 2018/0353334 A1 | 12/2018 | Locke et al. |
| 2018/0353337 A1 | 12/2018 | Locke |
| 2018/0353339 A1 | 12/2018 | Locke et al. |

(56) References Cited

U.S. PATENT DOCUMENTS

| | | |
|---|---|---|
| 2018/0353340 A1 | 12/2018 | Robinson et al. |
| 2018/0353344 A1 | 12/2018 | Locke et al. |
| 2018/0353662 A1 | 12/2018 | Locke et al. |
| 2018/0353663 A1 | 12/2018 | Locke et al. |
| 2018/0360667 A1 | 12/2018 | Droche |
| 2019/0000677 A1 | 1/2019 | Munro |
| 2019/0015258 A1 | 1/2019 | Gowans et al. |
| 2019/0015468 A1 | 1/2019 | Yadav et al. |
| 2019/0030223 A1 | 1/2019 | Lin |
| 2019/0046682 A1 | 2/2019 | Choi et al. |
| 2019/0060127 A1 | 2/2019 | Locke et al. |
| 2019/0083752 A1 | 3/2019 | Howell et al. |
| 2019/0117465 A1 | 4/2019 | Osborne et al. |
| 2019/0117466 A1 | 4/2019 | Kazala, Jr. et al. |
| 2019/0117861 A1 | 4/2019 | Locke et al. |
| 2019/0125590 A1 | 5/2019 | Rehbein et al. |
| 2019/0133830 A1 | 5/2019 | Bishop et al. |
| 2019/0151155 A1 | 5/2019 | Bonn |
| 2019/0151159 A1 | 5/2019 | Gowans et al. |
| 2019/0151495 A1 | 5/2019 | Helary et al. |
| 2019/0184052 A1 | 6/2019 | Ilan et al. |
| 2019/0231600 A1 | 8/2019 | Locke et al. |
| 2019/0231602 A1 | 8/2019 | Locke et al. |
| 2019/0231943 A1 | 8/2019 | Robinson et al. |
| 2019/0274889 A1 | 9/2019 | Steward et al. |
| 2019/0282728 A1 | 9/2019 | Kellar et al. |
| 2019/0290799 A1 | 9/2019 | Arshi et al. |
| 2019/0298249 A1 | 10/2019 | Bates et al. |
| 2019/0298577 A1 | 10/2019 | Locke et al. |
| 2019/0298578 A1 | 10/2019 | Shulman et al. |
| 2019/0298579 A1 | 10/2019 | Moore et al. |
| 2019/0298580 A1 | 10/2019 | Hall et al. |
| 2019/0298582 A1 | 10/2019 | Addison et al. |
| 2019/0298881 A1 | 10/2019 | Ramjit et al. |
| 2019/0298882 A1 | 10/2019 | Nelson |
| 2019/0298895 A1 | 10/2019 | Selby et al. |
| 2019/0307611 A1 | 10/2019 | Askem et al. |
| 2019/0307612 A1 | 10/2019 | Hartwell et al. |
| 2019/0307934 A1 | 10/2019 | Allen et al. |
| 2019/0307935 A1 | 10/2019 | Simmons et al. |
| 2019/0314187 A1 | 10/2019 | Emslander et al. |
| 2019/0314209 A1 | 10/2019 | Ha et al. |
| 2019/0314544 A1 | 10/2019 | Filho et al. |
| 2019/0321232 A1 | 10/2019 | Jardret et al. |
| 2019/0321509 A1 | 10/2019 | Chakravarthy et al. |
| 2019/0321526 A1 | 10/2019 | Robinson et al. |
| 2019/0322795 A1 | 10/2019 | Kubo et al. |
| 2019/0328580 A1 | 10/2019 | Emslander et al. |
| 2019/0336343 A1 | 11/2019 | Etchells et al. |
| 2019/0336344 A1 | 11/2019 | Locke |
| 2019/0336345 A1 | 11/2019 | Bannwart |
| 2019/0336346 A1 | 11/2019 | Locke et al. |
| 2019/0336640 A1 | 11/2019 | Vismara et al. |
| 2019/0336641 A1 | 11/2019 | Nisbet |
| 2019/0336643 A1 | 11/2019 | Luukko et al. |
| 2019/0336658 A1 | 11/2019 | Heaton et al. |
| 2019/0336739 A1 | 11/2019 | Locke et al. |
| 2019/0343687 A1 | 11/2019 | Locke et al. |
| 2019/0343889 A1 | 11/2019 | Luukko et al. |
| 2019/0343979 A1 | 11/2019 | Kearney et al. |
| 2019/0343993 A1 | 11/2019 | Weston |
| 2019/0343994 A1 | 11/2019 | Greener |
| 2019/0344242 A1 | 11/2019 | Kim et al. |
| 2019/0350763 A1 | 11/2019 | Pratt et al. |
| 2019/0350764 A1 | 11/2019 | Zochowski et al. |
| 2019/0350765 A1 | 11/2019 | Heagle et al. |
| 2019/0350775 A1 | 11/2019 | Biasutti et al. |
| 2019/0350970 A1 | 11/2019 | Saphier et al. |
| 2019/0351092 A1 | 11/2019 | Silver et al. |
| 2019/0351093 A1 | 11/2019 | Stein et al. |
| 2019/0351094 A1 | 11/2019 | Maher et al. |
| 2019/0351095 A1 | 11/2019 | Maher et al. |
| 2019/0351111 A1 | 11/2019 | Locke et al. |
| 2019/0358088 A1 | 11/2019 | Lavocah et al. |
| 2019/0358361 A1 | 11/2019 | McInnes et al. |
| 2019/0358372 A1 | 11/2019 | Askem et al. |
| 2019/0365948 A1 | 12/2019 | Deegan et al. |
| 2019/0365962 A1 | 12/2019 | Lee et al. |
| 2019/0374408 A1 | 12/2019 | Robles et al. |
| 2019/0374673 A1 | 12/2019 | Hoefinghoff et al. |
| 2019/0380878 A1 | 12/2019 | Edwards et al. |
| 2019/0380881 A1 | 12/2019 | Albert et al. |
| 2019/0380882 A1 | 12/2019 | Taylor et al. |
| 2019/0380883 A1 | 12/2019 | Macphee et al. |
| 2019/0381222 A9 | 12/2019 | Locke et al. |
| 2019/0388577 A1 | 12/2019 | Chandrashekhar-Bhat et al. |
| 2019/0388579 A1 | 12/2019 | Macphee et al. |
| 2019/0388589 A1 | 12/2019 | Macphee et al. |
| 2020/0000640 A1 | 1/2020 | Mondal et al. |
| 2020/0000642 A1 | 1/2020 | Waite |
| 2020/0000955 A1 | 1/2020 | Andrews et al. |
| 2020/0000956 A1 | 1/2020 | Huang et al. |
| 2020/0000985 A1 | 1/2020 | Seddon et al. |
| 2020/0008981 A1 | 1/2020 | Wheldrake |
| 2020/0009289 A1 | 1/2020 | Torabinejad et al. |
| 2020/0009400 A1 | 1/2020 | Ribeiro et al. |
| 2020/0017650 A1 | 1/2020 | Young et al. |
| 2020/0022844 A1 | 1/2020 | Blott et al. |
| 2020/0023102 A1 | 1/2020 | Powell |
| 2020/0023103 A1 | 1/2020 | Joshi et al. |
| 2020/0023104 A1 | 1/2020 | Eriksson et al. |
| 2020/0023105 A1 | 1/2020 | Long et al. |
| 2020/0023106 A1 | 1/2020 | Carroll et al. |
| 2020/0030153 A1 | 1/2020 | Johannison et al. |
| 2020/0030480 A1 | 1/2020 | Choi |
| 2020/0030499 A1 | 1/2020 | Menon et al. |
| 2020/0038023 A1 | 2/2020 | Dunn |
| 2020/0038249 A1 | 2/2020 | Pratt et al. |
| 2020/0038250 A1 | 2/2020 | Edwards et al. |
| 2020/0038251 A1 | 2/2020 | Locke et al. |
| 2020/0038252 A1 | 2/2020 | Spiro |
| 2020/0038283 A1 | 2/2020 | Hall et al. |
| 2020/0038470 A1 | 2/2020 | Datt et al. |
| 2020/0038544 A1 | 2/2020 | Grover et al. |
| 2020/0038546 A1 | 2/2020 | Dizio et al. |
| 2020/0038639 A1 | 2/2020 | Patel et al. |
| 2020/0046565 A1 | 2/2020 | Barta et al. |
| 2020/0046566 A1 | 2/2020 | Carey et al. |
| 2020/0046567 A1 | 2/2020 | Carroll et al. |
| 2020/0046568 A1 | 2/2020 | Sexton |
| 2020/0046663 A1 | 2/2020 | Murdock et al. |
| 2020/0046876 A1 | 2/2020 | Liu |
| 2020/0046887 A1 | 2/2020 | Runquist et al. |
| 2020/0054491 A1 | 2/2020 | Hentrich et al. |
| 2020/0054781 A1 | 2/2020 | Weiser et al. |
| 2020/0060879 A1 | 2/2020 | Edwards et al. |
| 2020/0061253 A1 | 2/2020 | Long et al. |
| 2020/0061254 A1 | 2/2020 | Joshi et al. |
| 2020/0061379 A1 | 2/2020 | Bogie et al. |
| 2020/0064220 A1 | 2/2020 | Locke |
| 2020/0069183 A1 | 3/2020 | Rice et al. |
| 2020/0069476 A1 | 3/2020 | Randolph et al. |
| 2020/0069477 A1 | 3/2020 | Holm et al. |
| 2020/0069478 A1 | 3/2020 | Jabbarzadeh et al. |
| 2020/0069479 A1 | 3/2020 | Buan et al. |
| 2020/0069835 A1 | 3/2020 | Hissink et al. |
| 2020/0069850 A1 | 3/2020 | Beadle et al. |
| 2020/0069851 A1 | 3/2020 | Blott et al. |
| 2020/0069853 A1 | 3/2020 | Hall et al. |
| 2020/0078223 A1 | 3/2020 | Locke et al. |
| 2020/0078224 A1 | 3/2020 | Carroll et al. |
| 2020/0078225 A1 | 3/2020 | Grillitsch et al. |
| 2020/0078305 A1 | 3/2020 | Auvinen et al. |
| 2020/0078330 A1 | 3/2020 | Gay |
| 2020/0078482 A1 | 3/2020 | Yoon et al. |
| 2020/0078499 A1 | 3/2020 | Gadde et al. |
| 2020/0085625 A1 | 3/2020 | Bellini et al. |
| 2020/0085626 A1 | 3/2020 | Braga et al. |
| 2020/0085629 A1 | 3/2020 | Locke et al. |
| 2020/0085630 A1 | 3/2020 | Robinson et al. |
| 2020/0085632 A1 | 3/2020 | Locke et al. |
| 2020/0085991 A1 | 3/2020 | Coomber |
| 2020/0085992 A1 | 3/2020 | Locke et al. |
| 2020/0086014 A1 | 3/2020 | Locke et al. |

(56) References Cited

U.S. PATENT DOCUMENTS

| | | |
|---|---|---|
| 2020/0086017 A1 | 3/2020 | Jardret et al. |
| 2020/0086049 A1 | 3/2020 | Park et al. |
| 2020/0093646 A1 | 3/2020 | Locke et al. |
| 2020/0093756 A1 | 3/2020 | Sabacinski |
| 2020/0093953 A1 | 3/2020 | Kim et al. |
| 2020/0093954 A1 | 3/2020 | Leise, III |
| 2020/0093970 A1 | 3/2020 | Hunt et al. |
| 2020/0095421 A1 | 3/2020 | Kettel |
| 2020/0095620 A1 | 3/2020 | Kellar et al. |
| 2020/0100945 A1 | 4/2020 | Albert et al. |
| 2020/0107964 A1 | 4/2020 | Locke et al. |
| 2020/0107965 A1 | 4/2020 | Greener |
| 2020/0107967 A1 | 4/2020 | Holm et al. |
| 2020/0108169 A1 | 4/2020 | Hu et al. |
| 2020/0113741 A1 | 4/2020 | Rehbein et al. |
| 2020/0114039 A1 | 4/2020 | Wang et al. |
| 2020/0114040 A1 | 4/2020 | Waite et al. |
| 2020/0114049 A1 | 4/2020 | Wall |
| 2020/0121510 A1 | 4/2020 | Hartwell et al. |
| 2020/0121521 A1 | 4/2020 | Daniel et al. |
| 2020/0121833 A9 | 4/2020 | Askem et al. |
| 2020/0129338 A1 | 4/2020 | Gardiner et al. |
| 2020/0129341 A1 | 4/2020 | Coulthard et al. |
| 2020/0129654 A1 | 4/2020 | Bouvier et al. |
| 2020/0129655 A1 | 4/2020 | Gardiner et al. |
| 2020/0129675 A1 | 4/2020 | Robinson et al. |
| 2020/0138754 A1 | 5/2020 | Johnson |
| 2020/0139023 A1 | 5/2020 | Haggstrom et al. |
| 2020/0139025 A1 | 5/2020 | Robinson et al. |
| 2020/0141031 A1 | 5/2020 | Kosan et al. |
| 2020/0146894 A1 | 5/2020 | Long et al. |
| 2020/0155355 A1 | 5/2020 | Hill et al. |
| 2020/0155358 A1 | 5/2020 | Wheldrake |
| 2020/0155361 A1 | 5/2020 | Pigg et al. |
| 2020/0155379 A1 | 5/2020 | Shaw et al. |
| 2020/0163802 A1 | 5/2020 | Hunt et al. |
| 2020/0163803 A1 | 5/2020 | Pigg et al. |
| 2020/0164112 A1 | 5/2020 | Kato et al. |
| 2020/0164120 A1 | 5/2020 | Jaecklein et al. |
| 2020/0170841 A1 | 6/2020 | Waite et al. |
| 2020/0170842 A1 | 6/2020 | Locke |
| 2020/0170843 A1 | 6/2020 | Collinson et al. |
| 2020/0171197 A1 | 6/2020 | Hubbell et al. |
| 2020/0179558 A1 | 6/2020 | Munro et al. |
| 2020/0179673 A1 | 6/2020 | Wan |
| 2020/0188180 A1 | 6/2020 | Akbari et al. |
| 2020/0188182 A1 | 6/2020 | Sanders et al. |
| 2020/0188550 A1 | 6/2020 | Dagger et al. |
| 2020/0188564 A1 | 6/2020 | Dunn |
| 2020/0190310 A1 | 6/2020 | Meyer |
| 2020/0197227 A1 | 6/2020 | Locke et al. |
| 2020/0197228 A1 | 6/2020 | Hartwell |
| 2020/0197559 A1 | 6/2020 | Bourdillon et al. |
| 2020/0197580 A1 | 6/2020 | Kilpadi et al. |
| 2020/0206036 A1 | 7/2020 | Robinson et al. |
| 2020/0214637 A1 | 7/2020 | Brownhill et al. |
| 2020/0214897 A1 | 7/2020 | Long et al. |
| 2020/0214898 A1 | 7/2020 | Waite et al. |
| 2020/0215220 A1 | 7/2020 | Schomburg et al. |
| 2020/0215226 A1 | 7/2020 | Kitagawa et al. |
| 2020/0222469 A1 | 7/2020 | Cotton |
| 2020/0229983 A1 | 7/2020 | Robinson et al. |
| 2020/0237564 A1 | 7/2020 | Hammond et al. |
| 2020/0237816 A1 | 7/2020 | Lait |
| 2020/0246195 A1 | 8/2020 | Robinson et al. |
| 2020/0253785 A1 | 8/2020 | Bernet et al. |
| 2020/0253786 A1 | 8/2020 | Harrison et al. |
| 2020/0254139 A1 | 8/2020 | Phillips et al. |
| 2020/0261275 A1 | 8/2020 | Manwaring et al. |
| 2020/0261276 A1 | 8/2020 | Lujan Hernandez et al. |
| 2020/0268560 A1 | 8/2020 | Harrison et al. |
| 2020/0268561 A1 | 8/2020 | Locke et al. |
| 2020/0270484 A1 | 8/2020 | Lipscomb et al. |
| 2020/0276055 A1 | 9/2020 | Randolph et al. |
| 2020/0276058 A1 | 9/2020 | Locke et al. |
| 2020/0277450 A1 | 9/2020 | Silverstein et al. |
| 2020/0281519 A1 | 9/2020 | Gowans et al. |
| 2020/0281529 A1 | 9/2020 | Grubb et al. |
| 2020/0281678 A1 | 9/2020 | Long et al. |
| 2020/0281775 A1 | 9/2020 | Kushnir et al. |
| 2020/0282100 A1 | 9/2020 | Gil et al. |
| 2020/0282114 A1 | 9/2020 | Long et al. |
| 2020/0282115 A1 | 9/2020 | Gardner et al. |
| 2020/0289328 A1 | 9/2020 | Luckemeyer et al. |
| 2020/0289347 A1 | 9/2020 | Gowans et al. |
| 2020/0289701 A1 | 9/2020 | Hall et al. |
| 2020/0289712 A1 | 9/2020 | Jiang et al. |
| 2020/0289723 A1 | 9/2020 | Gregory |
| 2020/0289726 A1 | 9/2020 | Locke et al. |
| 2020/0289727 A1 | 9/2020 | Locke |
| 2020/0289806 A1 | 9/2020 | Locke et al. |
| 2020/0297541 A1 | 9/2020 | Hartwell et al. |
| 2020/0297543 A1 | 9/2020 | Rodzewicz et al. |
| 2020/0297544 A1 | 9/2020 | Moine et al. |
| 2020/0297892 A1 | 9/2020 | Silcock |
| 2020/0297893 A1 | 9/2020 | Ericson |
| 2020/0297894 A1 | 9/2020 | Koyama et al. |
| 2020/0299865 A1 | 9/2020 | Bonnefin et al. |
| 2020/0306089 A1 | 10/2020 | Delury et al. |
| 2020/0306091 A1 | 10/2020 | Lee et al. |
| 2020/0306094 A1 | 10/2020 | Kushnir et al. |
| 2020/0315853 A1 | 10/2020 | Waite |
| 2020/0315854 A1 | 10/2020 | Simmons et al. |
| 2020/0316271 A1 | 10/2020 | Lin |
| 2020/0323692 A1 | 10/2020 | Locke et al. |
| 2020/0324015 A1 | 10/2020 | Kettel et al. |
| 2020/0330283 A1 | 10/2020 | Locke et al. |
| 2020/0330284 A1 | 10/2020 | Locke et al. |
| 2020/0330285 A1 | 10/2020 | Rehbein et al. |
| 2020/0330658 A1 | 10/2020 | Fujisaki |
| 2020/0330660 A1 | 10/2020 | Patel et al. |
| 2020/0337719 A1 | 10/2020 | Ingram et al. |
| 2020/0337904 A1 | 10/2020 | Waite |
| 2020/0337905 A1 | 10/2020 | Earl et al. |
| 2020/0337906 A1 | 10/2020 | Long et al. |
| 2020/0337908 A1 | 10/2020 | Long et al. |
| 2020/0338228 A1 | 10/2020 | Kharkar et al. |
| 2020/0338243 A1 | 10/2020 | Harrison et al. |

FOREIGN PATENT DOCUMENTS

| | | |
|---|---|---|
| EP | 3187204 A1 | 7/2017 |
| GB | 738722 A | 10/1955 |
| WO | WO-9312275 A1 | 6/1993 |
| WO | WO-9416746 A1 | 8/1994 |
| WO | WO-0001425 A1 | 1/2000 |
| WO | 2005018543 A2 | 3/2005 |
| WO | WO-2007003905 A1 | 1/2007 |
| WO | 2011121394 A1 | 10/2011 |
| WO | 2011135284 A1 | 11/2011 |
| WO | 2011144888 A1 | 11/2011 |
| WO | 2013015827 A2 | 1/2013 |
| WO | 2013126049 A1 | 8/2013 |
| WO | 2014014842 A1 | 1/2014 |
| WO | 2015145117 A1 | 10/2015 |
| WO | 2015173546 A1 | 11/2015 |
| WO | 2016141450 A1 | 9/2016 |
| WO | 2017016974 A1 | 2/2017 |
| WO | 2017125250 A1 | 7/2017 |
| WO | 2018029231 A1 | 2/2018 |
| WO | 2018094061 A1 | 5/2018 |
| WO | 2018162613 A1 | 9/2018 |
| WO | 2018163093 A1 | 9/2018 |
| WO | 2018189265 A1 | 10/2018 |
| WO | 2018226667 A1 | 12/2018 |
| WO | 2018227144 A1 | 12/2018 |
| WO | 2018231825 A1 | 12/2018 |
| WO | 2018236648 A1 | 12/2018 |
| WO | 2019002085 A1 | 1/2019 |
| WO | 2019012068 A1 | 1/2019 |
| WO | 2019012069 A1 | 1/2019 |
| WO | 2019022493 A1 | 1/2019 |
| WO | 2019027933 A1 | 2/2019 |
| WO | 2019038548 A1 | 2/2019 |

(56) References Cited

FOREIGN PATENT DOCUMENTS

| | | |
|---|---|---|
| WO | 2019038549 A1 | 2/2019 |
| WO | 2019040656 A1 | 2/2019 |
| WO | 2019050855 A1 | 3/2019 |
| WO | 2019058373 A1 | 3/2019 |
| WO | 2019073326 A1 | 4/2019 |
| WO | 2019083563 A1 | 5/2019 |
| WO | 2019083868 A1 | 5/2019 |
| WO | 2019086911 A1 | 5/2019 |
| WO | 2019091150 A1 | 5/2019 |
| WO | 2019094147 A1 | 5/2019 |
| WO | 2019096828 A1 | 5/2019 |
| WO | 2019113275 A1 | 6/2019 |
| WO | 2019113623 A1 | 6/2019 |
| WO | 2019191590 A1 | 10/2019 |
| WO | 2019193141 A1 | 10/2019 |
| WO | 2019193333 A1 | 10/2019 |
| WO | 2019199389 A1 | 10/2019 |
| WO | 2019199596 A1 | 10/2019 |
| WO | 2019199687 A1 | 10/2019 |
| WO | 2019199798 A1 | 10/2019 |
| WO | 2019199849 A1 | 10/2019 |
| WO | 2019200035 A1 | 10/2019 |
| WO | 2019215572 A1 | 11/2019 |
| WO | 2019219613 A1 | 11/2019 |
| WO | 2019234365 A1 | 12/2019 |
| WO | 2020005062 A1 | 1/2020 |
| WO | 2020005344 A1 | 1/2020 |
| WO | 2020005536 A1 | 1/2020 |
| WO | 2020005546 A1 | 1/2020 |
| WO | 2020005577 A1 | 1/2020 |
| WO | 2020007429 A1 | 1/2020 |
| WO | 2020011691 A1 | 1/2020 |
| WO | 2020014178 A1 | 1/2020 |
| WO | 2020014310 A1 | 1/2020 |
| WO | 2020018300 A1 | 1/2020 |
| WO | 2020026061 A1 | 2/2020 |
| WO | 2020026144 A1 | 2/2020 |
| WO | 2020033351 A1 | 2/2020 |
| WO | 2020035811 A1 | 2/2020 |
| WO | 2020043665 A1 | 3/2020 |
| WO | 2020044237 A1 | 3/2020 |
| WO | 2020046443 A1 | 3/2020 |
| WO | 2020047255 A1 | 3/2020 |
| WO | 2020049038 A1 | 3/2020 |
| WO | 2020055945 A1 | 3/2020 |
| WO | 2020056182 A1 | 3/2020 |
| WO | 2020056914 A1 | 3/2020 |

OTHER PUBLICATIONS

Dillon, J.M. et al. The Jubilee method a modern dressing design which reduces complications and improves cost-effectiveness following total hip and knee arthroplasty. 8th European Federation of National Associations of Orthopaedics and Traumatology Congress, May 11, 2007. Glaslow.
No Author. BS EN 13726-1: 2002 Test Methods for Primary Wound Dressings Part 1: Aspects of absorbency, (pp. 1-20) (Apr. 15, 2002).
U.S. Appl. No. 13/120,733 Office Action dated Jun. 1, 2017.
U.S. Appl. No. 13/120,733 Office Action dated Mar. 22, 2016.
U.S. Appl. No. 13/120,733 Office Action dated Nov. 17, 2016.
U.S. Appl. No. 13/120,733 Office Action dated Nov. 8, 2017.
White, Sarah E. Yarn Over, About Home. http://knitting.about.com./od/knittingglossary/g/yarn_over.htm (Oct. 29, 2007).
Worst, Edward. Problems in Raffia. Industrial Education. Volume 8. CCM Professional Magazines, Inc. 1919, p. 183.

* cited by examiner

WOUND DRESSING

CROSS-REFERENCE

This application is a continuation of U.S. application Ser. No. 13/120,733, filed Aug. 8, 2011, which is the U.S. National Stage Entry of International Application No. PCT/GB2009/002342, filed Sep. 29, 2009, which claims priority to United Kingdom Application No. 0817796.6, filed on Sep. 29, 2008, all of which are incorporated herein by reference their entireties.

This invention relates to a wound dressing, in particular to wound dressings for use on post surgical sites. The invention preferably relates to dressings comprising gel forming fibres used on sites requiring a high degree of conformability and resilience such as those on the hip or knee following orthopaedic surgery.

Wounds on post operative sites such as those following knee or hip surgery can suffer problems with blistering of the skin around the incision site and infection. In addition frequent dressing changes may be necessary due to copious discharge produced at the site.

It is known to use carboxymethylated cellulosic materials in situations where a high degree of exudate absorption is required. For example, WO 93/12275 describes the production of various absorbent products capable of absorbing many times their own weight of water. This causes the carboxymethylated fibres to form a gel. WO 94/16746 and WO 00/01425 describe the use of carboxymethylated Lyocell materials in wound dressings where the advantages of gel formation in preventing adherence and therefore reducing wound damage and pain on removal are discussed.

It is also known to use carboxymethylated cellulosic fibres in the form of a fabric in combination with an adhesive layer to treat post surgical sites. For example, it is known to use Aquacel® (a dressing made of carboxymethylated cellulosic fibres and sold by ConvaTec) combined with Duoderm® Extra Thin® (an occlusive exterior layer which is also adhesive) on post surgical sites in a method reported as the Jubilee method where an Aquacel® island in the form of a narrow strip is surrounded at its periphery with an overlying layer of Duoderm Extra Thin which secures the dressing to the site (The Jubilee Method: a modern dressing design which reduces complications and is cost-effective following total knee and hip arthroplasty. Dillon J. M., Clarke, J. V. et al. Dept of Orthopaedics, Golden Jubilee National Hospital Glasgow EWMA2007, Glasgow).

Although such a combination of advanced dressing materials provides advances over a traditional gauze dressing in that for instance blistering and infection are reduced, post surgical sites have specific needs that remain to be addressed. For instance, dressings for use on the knee or hip following arthroplasty or those on sites where there is a wide range of patient movement require high conformability and resilience from the dressing otherwise patient movement is restricted and blistering occurs due to friction between the dressing and the skin. Most absorbent pads are unable to stretch and so delaminate on flexion of the knee or joint. Even gel-forming dressings break down with repeated movement of the limb. The non-woven fabric of Aquacel®, although conformable and flexible can tend to shrink on absorption of exudate making it less able to bend and stretch. It would be desirable to bring the advantages of gel forming dressings to surgical sites by having the dressings available in a form with a reduced tendency to shrink and an ability for all the layers to stretch and recover so that the dressing accommodates the normal movement of the joint during wear.

It is known to increase the tensile strength of bandages by stitching the bandage longitudinally with one or more lines of stitches. WO 2007/003905 describes such dressings which are particularly suitable for use in dressing burns.

We have found that it is possible to improve the resilience of dressings to mitigate the problems associated with dressing post operative sites where movement occurs.

Accordingly the invention provides a wound dressing comprising an absorbent layer, the absorbent layer being gathered in a longitudinal direction by one or more resilient yarns.

By resilient is meant that the yarn or thread is able to extend and contract to its former shape. The gathers in the absorbent layer formed by the resilient thread or yarn, enable the absorbent layer to extend and contract with movement so that when, for example, the patient's leg is bent the dressing stretches and when the leg is straightened, the dressing recovers its former size. This resilience means that the absorbent layer maintains close conformability with the wound during movement of the patient. It also means that the dressing has a reduced tendency to delaminate during wear. Having the ability to stretch means that there is less movement between the dressing and the patient which reduces blistering.

Preferably the dressing further comprises an adhesive layer overlying the absorbent layer on a surface furthest from the wound in use and extending beyond the periphery of the absorbent layer so as to secure the dressing to the skin.

Preferably the absorbent layer further comprises lines of longitudinal warp stitches formed from an inelastic thread which stitching is longitudinal in that it is generally parallel to the long dimension of the absorbent layer. The warp stitches are preferably made in the absorbent layer after it has been formed.

The inelastic warp stitching preferably passes through the whole thickness of the absorbent layer and is visible on both sides. The absorbent layer preferably comprises two or more layers of fabric that are layered together and stitch bonded with lines of longitudinal inelastic warp stitches. The resilient thread is preferably woven in between the stitches of the inelastic warp stitching and in between the sheets of fabric. By having two layers of fabric it is possible to hold the resilient thread or yarn out of direct contact with the wound.

The resilient thread gathers the absorbent layer and enables it to elongate and then return to shape. The resilient thread can be stitched through the absorbent layer to gather the dressing or woven through a separate line of inelastic warp stitches. The resilient thread can be stitched through the absorbent layer in lines of longitudinal stitches 1 mm to 10 mm apart, more preferably 2 mm to 5 mm apart. The resilient thread is preferably applied to the absorbent layer after the absorbent layer has been formed.

The absorbent layer preferably has an absorbency of at least 2 grams of of 0.9% saline solution per gram of fabric as measured by the free swell method. The absorbent layer preferably comprises gel forming fibres. By gel forming is meant hygroscopic fibres which upon the uptake of wound exudate become moist slippery or gelatinous and thus reduce the tendency for the surrounding fibres to adhere to the wound. The gel forming fibres can be of the type which retain their structural integrity on absorption of exudate or can be of the type which lose their fibrous form and become a structureless gel. The gel forming fibres are preferably spun sodium carboxymethylcellulose fibres, chemically modified cellulosic fibres, pectin fibres, alginate fibres, chitosan fibres, hyaluronic acid fibres, or other polysaccharide fibres or fibres derived from gums. The cellulosic fibres preferably have a degree of substitution of at least 0.05 carboxymethyl groups per glucose unit. The gel forming fibres preferably have an absorbency of at least 2 grams 0.9% saline solution per gram of fibre (as measured by the free swell method).

Preferably the gel forming fibres have an absorbency of at least 10 g/g as measured in the free swell absorbency method, more preferably, between 15 g/g and 25 g/g.

Carboxymethylation can be achieved, for example, by sequential or simultaneous treatment of the cellulosic material with a strong alkali, such as aqueous sodium hydroxide, and monochloroacetic acid or a salt thereof. The appropriate reaction conditions will depend upon the composition of the fabric and the degree of carboxymethylation required and will be readily apparent to the person skilled in the art. They may be identical or similar to those described in WO 93/12275, WO 94/16746 or WO 00/01425 to which the reader is directed for further detail.

Desirably the carboxymethylation is carried out in the presence of industrial methylated spirits (IMS), and IMS is preferably also used in a subsequent washing step, suitably along with water, as a cleaner and steriliser. The degree of carboxymethylation is desirably such that upon absorption of exudate the fibres at the skin-contacting surface of the bandage form a gel.

The dressing may for instance comprise non gel forming fibres and in particular may comprise Linel, Lycra® or other elastic fibre.

The dressing may be in the form of a rectangle and be available in the following sizes, 9 cm×10 cm, 9 cm×15 cm, 9 cm×25 cm, 9 cm×35 cm. The lines of inelastic warp stitching may be from 1 mm to 10 mm apart and preferably from 2 mm to 5 mm apart. The lines of inelastic stitching are typically crocheted or knitted and have the appearance of a chain stitch but other stitch patterns may also be used. Preferably, the lines of resilient stitching gather the absorbent layer so that the absorbent layer is able to elongate by 25% to 85%, more preferably 35% to 75% and most preferably 40% to 70% and then recover even when the absorbent layer is hydrated. More preferably, the lines of warp stitching are made in a yarn or thread such as nylon or polyester or Tencel™ or any thread which is strong and easily processed. The resilient stitches are made in a resilient yarn such as an elastomeric yarn or linel or Lycra® or yarn which has good stretch and recovery or an elastane yarn which is an elastomeric yarn with greater than 85% polyurethane such as linel or Lycra® or Spandex.

The dressing may comprise a further adhesive layer overlying the first adhesive layer but on the opposite side of the absorbent layer. Preferably the adhesive layer includes a reinforcing scrim of polyurethane film to reduce any tendency of the adhesive to delaminate on dressing removal. The further adhesive layer preferably has a window cut from it that coincides with the absorbent layer and is present to hold the absorbent layer within the dressing and enable direct contact between the absorbent layer and the wound.

The adhesive layer may be of the type comprising a homogenous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatine, guar gum, locust bean gum, karaya gum, and mixtures thereof. The polyisobutylenes may be selected from low molecular weight polyisobutylenes having a viscosity average molecular weight of from 36,000 to 58,000 (Florey). The adhesive layer is capable of absorbing exudate while maintaining adhesion of the dressing to the skin.

Alternatively the adhesive composition may comprise a homogeneous blend of one or more hydrocolloids, one or more low molecular weight polyisobutylenes, one or more styrene block copolymers, mineral oil, butyl rubber, a tackifier and small amounts of optional components. By selection of specific ranges of the amounts of the above listed components, an adhesive composition may be prepared having good adhesion to the skin and stretchability. Such compositions and the preparation therefore are disclosed in EP-B-130061.

Preferably the adhesive is such that the removal of an adhesive wound dressing is not traumatic to the patient. Preferably the adhesive ensures a secure application of the dressing whist still permitting non-traumatic removal. Non-traumatic dressing removal may be facilitated by using an adhesive which gels slightly upon interaction with a fluid. The gel formation aiding dressing removal.

The absorbent layer may comprise one or more medicaments. For example an antimicrobial agent, or an antibiotic, or an anaesthetic on an anti-inflammatory agent or a skin protective agent or an odour absorbing agent.

In a further aspect the invention provides a method of manufacturing a wound dressing for use on post surgical wounds characterised in that the method comprises the steps of:

(i) forming an absorbent layer; and
(ii) gathering the absorbent layer with a resilient yarn.

Preferably the absorbent layer is formed first and is then stitched with a resilient yarn to gather it. The absorbent layer is preferably a layer of non woven gel forming fibres which is first formed and then stitch bonded with an inelastic yarn and a resilient yarn to gather it.

Figure 2:
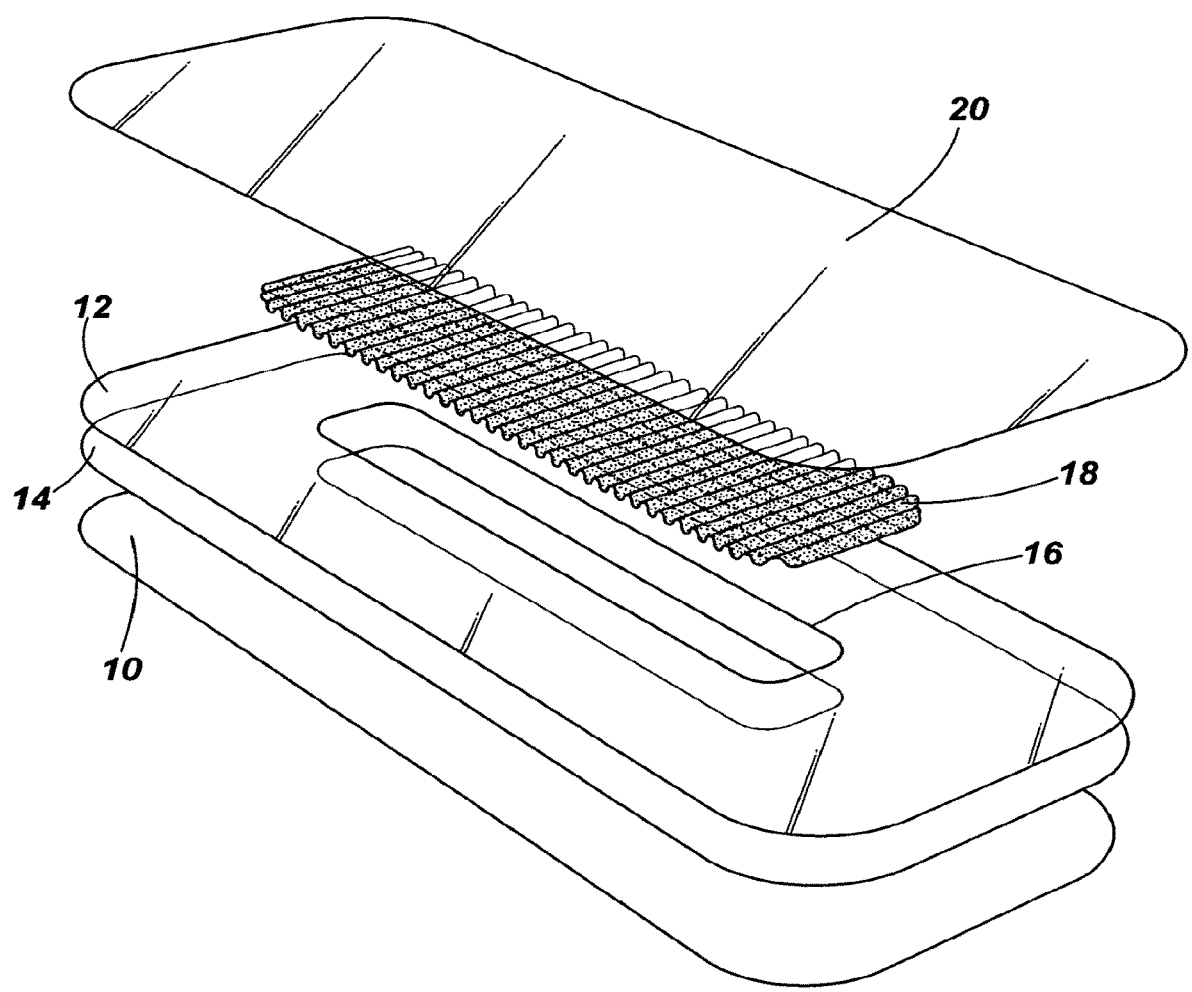

Preferred embodiments of the invention will now be described with reference to the accompanying drawings in which:

FIG. 1 is a view of a preferred embodiment of the dressing according to the invention in perspective view; and FIG. 2 is an exploded view of a further embodiment of the dressing according to the invention in perspective.

In FIG. 1 the dressing comprises a layer of hydrocolloid adhesive 2 onto which is bonded an absorbent layer 4. A further layer 6 of hydrocolloid adhesive having a window 8 is applied over the absorbent layer so that the absorbent layer is sandwiched between the two adhesive layers with the window exposing the absorbent layer to the surgical site.

The absorbent layer is made from a non woven roll made by forming a web of Lyocell which is then hydroentangled. The web is then carboxymethylated by sequential or simultaneous treatment of the cellulosic material with a strong alkali, monochloroacetic acid or a salt thereof. Two webs of the resulting fabric are then fed into a stitch bonding machine and stitched simultaneously with lines of longitudinal stitching in an inelastic yarn and a resilient yarn woven in between the stitches and so secured at the centre of the webs. The resilient yarn gathers the absorbent layer (not shown) and is carried by the inelastic stitch bonded yarn. The resulting layer has a basis weight of 350 gm$^{-2}$.

In FIG. 2 the dressing comprises two layers of hydrocolloid adhesive 10, 12 reinforced by a polyurethane film 14 into which is cut a window 16. An absorbent layer 18 is positioned over the window and overlaps the adhesive layer around its margin. A further layer 20 of adhesive backed with a polyurethane film is applied over the absorbent layer so that the absorbent layer is sandwiched between the layers with the window 16 exposing the absorbent layer 18 to the surgical site.

The absorbent layer is made from a tow of carboxymethyl cellulose filaments which has been needlefelted. Two webs of the needlefelted tow are fed into a stitch bonding machine and stitched simultaneously with lines of longitudinal stitching as shown in FIG. 2 in inelastic yarn and with a resilient yarn woven inbetween the stitches and so secured at the centre of the webs.

In the context of the present invention the terms yarn and thread are used to interchangeably.

Preferred embodiments of the invention will now be described with reference to the following examples:

EXAMPLE 1

The absorbency of the dressing described in FIG. 1 was measured against the absorbency of a dressing used in the Jubilee method referenced above. The absorbencies of the dressings were measured using the method described in BS EN 13726-1:2002 Test Methods for Primary Wound Dressings—Part 1: Aspects of absorbency.

The results are shown below:

|  | Control, Jubilee method (4 layers of Aquacel and DuoDerm Extra Thin) | Dressing of FIG. 1 |
| --- | --- | --- |
| Fluid absorbed by dressing(g/10 cm$^2$) (24 hr) | 6.3 (5.9-6.8) | 6.9 (6.8-7.0) |
| Fluid handling capacity (g/10 cm$^2$) (24 hr) | 6.6 (6.2-7.2) | 7.4 (7.3-7.5) |

These results show that the dressing according to the invention with a gathered absorbent layer has an absorbency and fluid handling capacity equivalent to that of a dressing using four layers of the same absorbent material.

EXAMPLE 2

The resilience of the dressing of FIG. 1 was measured by hydrating the dressing with 30 ml of solution A which was coloured using blue food dye. Masking tape was adhered to the short ends of the dressing and the dressing fixed in the grips of a Zwick Universal Testing Machine. The distance between the grips was extended by 20% and the Zwick was set to run a cyclic test with a pause at maximum extension of 15 seconds and a pause at recovery of 60 seconds. The number of cycles was 1000 with a speed of travel of 250 mm per minute. After testing no breakdown of the dressing was seen. The dressing remained integral and retained all of the solution A added at the beginning of the test. The force required to extend a 25 cm dressing length was 10.76 N. The stretch as a percentage of the original dressing length was 20%.

These results suggest that the dressing may enable increased or easier limb movement during patient rehabilitation.

The invention claimed is:

1. A wound dressing comprising a nonwoven absorbent layer comprising a layer of fabric comprising gel-forming fibers, the absorbent layer being gathered in a longitudinal direction by stitching through the layer of fabric using one or more resilient threads or yarns and an inelastic thread or yarn, wherein the resilient and inelastic threads or yarns extend at least primarily in the longitudinal direction, and wherein the resilient and inelastic threads or yarns gather the layer of fabric so that the layer of fabric in use is configured to:
   (a) maintain close conformability with a wound during movement; and
   (b) elongate by 35% to 85% and then recover.

2. The wound dressing as claimed in claim 1 further comprising an adhesive layer overlying the absorbent layer on a surface furthest from the wound in use and extending beyond a periphery of the absorbent layer so as to secure the dressing to skin surrounding the wound.

3. The wound dressing as claimed in claim 1 characterised in that the resilient thread or yarn is woven in between the inelastic thread or yarn stitches to gather the absorbent layer.

4. The wound dressing of claim 1, wherein the layer of fabric is configured to fully recover after an elongation in the range of 35% to 85%.

5. The wound dressing of claim 1, wherein the gel-forming fibers are configured to retain structural integrity on absorption of exudate.

6. The wound dressing of claim 1, wherein the gel-forming fibers are configured to lose fibrous form and become a structureless gel upon absorption of exudate.

7. The wound dressing of claim 1, further comprising an inelastic warp stitch formed of the inelastic thread or yarn.

8. The wound dressing of claim 7, wherein the inelastic warp stitch extends in the longitudinal direction.

9. The wound dressing of claim 7, wherein the inelastic warp stitch passes through an entire thickness of the absorbent layer such that a first portion of the inelastic warp stitch is positioned on a first side of the absorbent layer and a second portion of the inelastic warp stitch is positioned on an opposite second side of the absorbent layer.

10. The wound dressing of claim 1, wherein the resilient and inelastic threads or yarns are parallel to one another.

11. A method of manufacturing the wound dressing of claim 1, wherein the method comprises the steps of:
   (i) forming the nonwoven absorbent layer comprising the layer of fabric comprising gel-forming fibers; and
   (ii) gathering the absorbent layer by stitching through the layer of fabric with the resilient thread or yarn and the inelastic thread or yarn, wherein the resilient and inelastic threads or yarns gather the layer of fabric so that the layer of fabric in use is configured to:
      (a) maintain close conformability with a wound during movement; and
      (b) elongate by 35% to 85% and then recover.

12. The method as claimed in claim 11 characterised in that the absorbent layer is formed from a non-woven fabric.

13. The method as claimed in claim 12 characterised in that the method comprises the further step of simultaneously weaving the resilient thread or yarn about the stitches of inelastic thread or yarn.

14. The method as claimed in claim 11, further comprising:
   (iii) overlying the absorbent layer with an adhesive layer on a surface furthest from the wound in use and extending beyond the periphery of the absorbent layer so as to adhere the dressing to the skin.

15. A wound dressing, comprising:
   a nonwoven absorbent layer comprising a layer of fabric comprising gel-forming fibers; and
   stitching that extends through the absorbent layer and that gathers the absorbent layer in a longitudinal direction, wherein the stitching comprises:

a resilient thread or yarn extending at least primarily in the longitudinal direction; and
an inelastic thread or yarn extending at least primarily in the longitudinal direction;
wherein the stitching gathers the layer of fabric such that the layer of fabric is configured to:
maintain close conformability with a wound during movement; and
elongate from an initial length by 35% to 85% and to thereafter recover to the initial length.

16. The wound dressing of claim 15, further comprising an adhesive layer overlying the absorbent layer and extending beyond a periphery of the absorbent layer.

17. The wound dressing of claim 15, wherein the gel-forming fibers are configured to retain structural integrity on absorption of exudate.

18. The wound dressing of claim 15, wherein the gel-forming fibers are configured to lose fibrous form and become a structureless gel upon absorption of exudate.

19. The wound dressing of claim 15, wherein the resilient thread or yarn is parallel to the inelastic thread or yarn.

* * * * *